United States Patent [19]

Haber et al.

[11] Patent Number: 5,376,087
[45] Date of Patent: Dec. 27, 1994

[54] MULTIPLE FUNCTION CAUTERIZING INSTRUMENT

[75] Inventors: Terry M. Haber, El Toro; William H. Smedley, Lake Elsinore; Clark B. Foster, Laguna Niguel, all of Calif.

[73] Assignee: Habley Medical Technology Corporation, Laguna Hills, Calif.

[21] Appl. No.: 934,129

[22] Filed: Aug. 21, 1992

[51] Int. Cl.5 .............................. A61B 17/39
[52] U.S. Cl. ........................... 606/27; 606/29; 606/45; 606/49
[58] Field of Search ................. 606/27–32, 606/37–42, 45, 46, 47

[56] References Cited

U.S. PATENT DOCUMENTS

| | | | |
|---|---|---|---|
| 2,102,270 | 12/1937 | Hyams | 606/49 |
| 3,850,162 | 11/1974 | Iglesias | 128/6 |
| 4,116,198 | 9/1978 | Roos | 606/46 |
| 4,362,160 | 12/1982 | Hiltebrandt | 606/49 X |
| 4,618,885 | 10/1986 | Nagasaki | 606/46 X |
| 4,919,129 | 4/1990 | Weber, Jr. et al. | 606/45 X |
| 5,035,231 | 7/1991 | Kubokawa et al. | 128/4 |
| 5,099,827 | 3/1992 | Melzer et al. | 128/6 X |
| 5,201,741 | 4/1993 | Dulebohn | 606/45 |

Primary Examiner—Peter A. Aschenbrenner
Attorney, Agent, or Firm—Hawes & Fischer

[57] ABSTRACT

A multiple function cauterizing instrument having a housing and an illuminating optical fiber extending from a lens, through the housing, to a high intensity light source for supplying incident light to the targeted tissue area to be cauterized. A viewing optical fiber extends from a wide angle camera lens, through the housing, to a video monitor for supplying to the monitor a visual image of the targeted tissue area. An exhaust channel extends from an intake vent, through the housing, to a source of vacuum to suction gas and fumes caused by cauterizing the tissue area. A plurality of heating elements or cauterizing tips are selectively moved through the housing between a retracted position at which the elements are shielded by the housing and an extended position at which the elements are advanced outwardly from the housing for contacting the tissue to be cauterized.

18 Claims, 7 Drawing Sheets

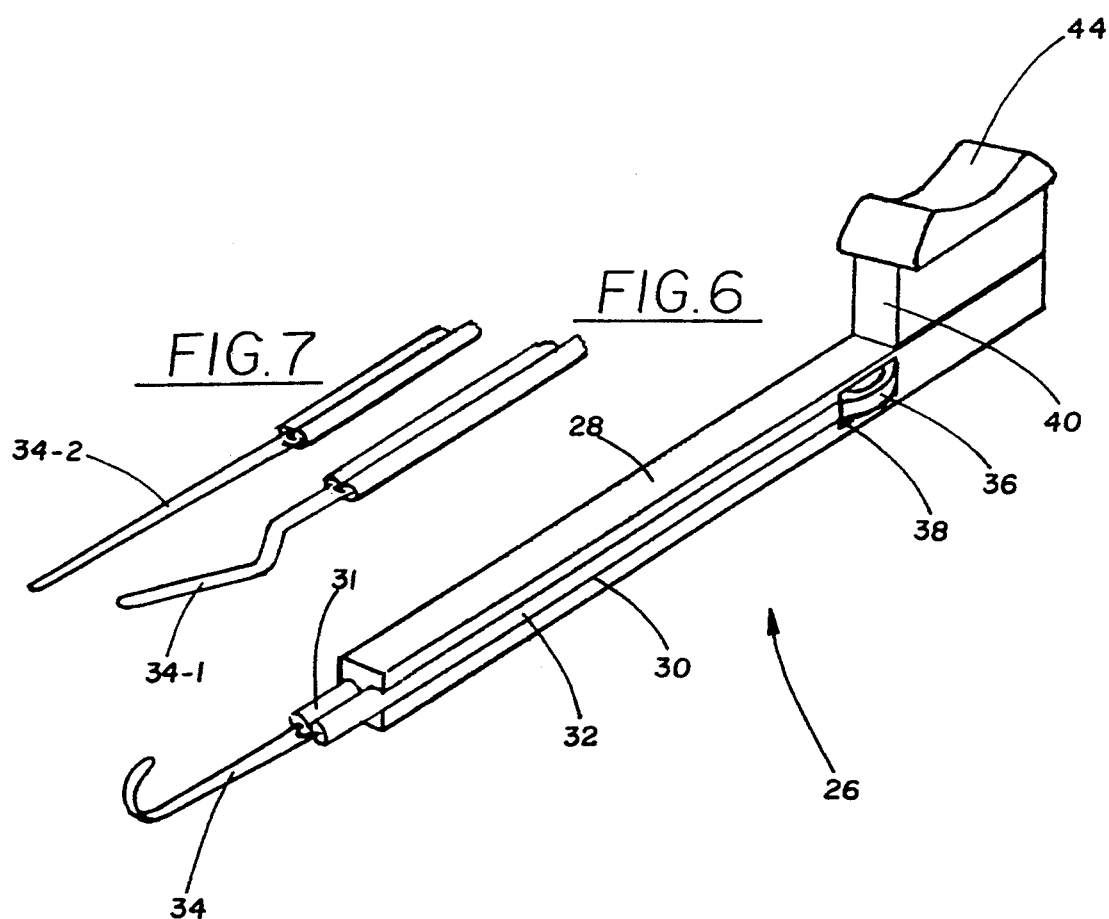

MULTIPLE FUNCTION CAUTERIZING INSTRUMENT

BACKGROUND OF THE INVENTION

1. Field of the Invention

This invention relates to a streamlined cauterizing instrument having optical viewing and illuminating means, gas and fume exhaust means, and a plurality of cauterizing tips to be selectively positioned and energized, all of which being efficiently carried within a common housing for use during a cauterizing procedure while producing minimum tissue trauma to the patient.

2. Background Art

Cauterizing tissue is a well known procedure that is often used during surgery. There are several reasons why a surgeon might wish to cauterize a patient's tissue. Typically, cauterizing is employed to close off bleeding as a consequence of surgery. Cauterizing has also been used to sterilize and cut tissue as well as to kill certain tissue that has been infected with disease such as cancer and the like.

Present cauterizing procedures are typically performed with a wand having a single cauterizing tip or heating element at one end. To accurately perform the procedure, the surgeon needs to be able to illuminate and view the local tissue area to be cauterized. If a different cauterizing tip is required, a separate wand must be used to accomplish the desired function. As a consequence of the foregoing, a plurality of viewing, illuminating and cauterizing tools are usually required to complete the cauterizing procedure. Moreover, the smoke and gas generated by burning tissue will sometimes obscure the surgeon's view. In this case, a separate venting tool is needed to suction the obstructions, whereby to permit the surgeon to have clear visual access to the targeted tissue area. What is more, an assistant is frequently needed in the operating room during the cauterizing procedure to manipulate the viewing means and coordinate the location of the cauterizing tip operated by the surgeon with the location of said viewing means.

The foregoing multiple operations to be performed with multiple tools during cauterizing a patient's tissue according to conventional techniques may be clumsy and require both visual and verbal communication between the surgeon and his assistant. In addition, the cauterizing operation may become inefficient and require the likelihood of several incisions and corresponding invasions into the patient's body cavity. This may cause excessive trauma to the patient's tissue while increasing the period necessary for recovery.

SUMMARY OF THE INVENTION

In general terms, a multiple function cauterizing instrument is disclosed having the ability to illuminate and view the targeted tissue area to be cauterized, exhaust gases and fumes from the target site, and selectively position a plurality of cauterizing elements or tips, all from a common housing. The cauterizing instrument includes an illumination optical fiber that extends through the housing between a lens at the nose of the instrument and a remote high intensity light source so that the targeted tissue area of the patient can be illuminated with incident light that is focused by the lens. The cauterizing instrument also includes a viewing optical fiber that extends through the housing between a wide angle camera lens at the nose of the instrument and a remote video display so that the surgeon may visualize the cauterization at the targeted tissue area. The cauterizing instrument further includes at least one exhaust channel that extends between an intake vent at the nose of the instrument and a remote vacuum source so that fumes and gases produced during the cauterizing process may be suctioned away from the target site so as not to obstruct the surgeon's view.

A plurality of guide rails are slidably received at respective guide channels which extend through the housing of the cauterizing instrument. Each guide rail carries a different cauterizing tip or heating element at one end thereof. Each guide rail also includes a pair of radially projecting electrical contacts that are adapted to be moved into contact with a corresponding pair of power terminals at opposite sides of a guide channel. A position control button is attached to a guide rail to enable the surgeon to selectively advance said guide rail through its guide channel for simultaneously advancing the cauterizing tip towards the targeted tissue area and moving the contacts of the guide rail into electrical connection with the power terminals of the guide channel. More particularly, in the at rest condition of the cauterizing instrument, all of the guide rails are retracted within their respective guide channels, such that the electrical contacts and power terminals are disconnected from one another and the cauterizing tips are shielded within the housing and de-energized. During the cauterizing process, any one of the guide rails may be selectively extended through its guide channel such that the electrical contacts of the guide rail are moved into connection with the power terminals of the guide channel. Accordingly, the cauterizing tip will be advanced outwardly of the housing and may be energized so as to enable the surgeon to efficiently and accurately complete the cauterizing process.

BRIEF DESCRIPTION OF THE DRAWINGS

FIG. 5 is a perspective view of one guide rail of the cauterizing instrument which carries a particular cauterizing tip;

FIGS. 6 and 7 show other cauterizing tips to be carried by respective guide rails of the cauterizing instrument;

DETAILED DESCRIPTION

Figure 1:
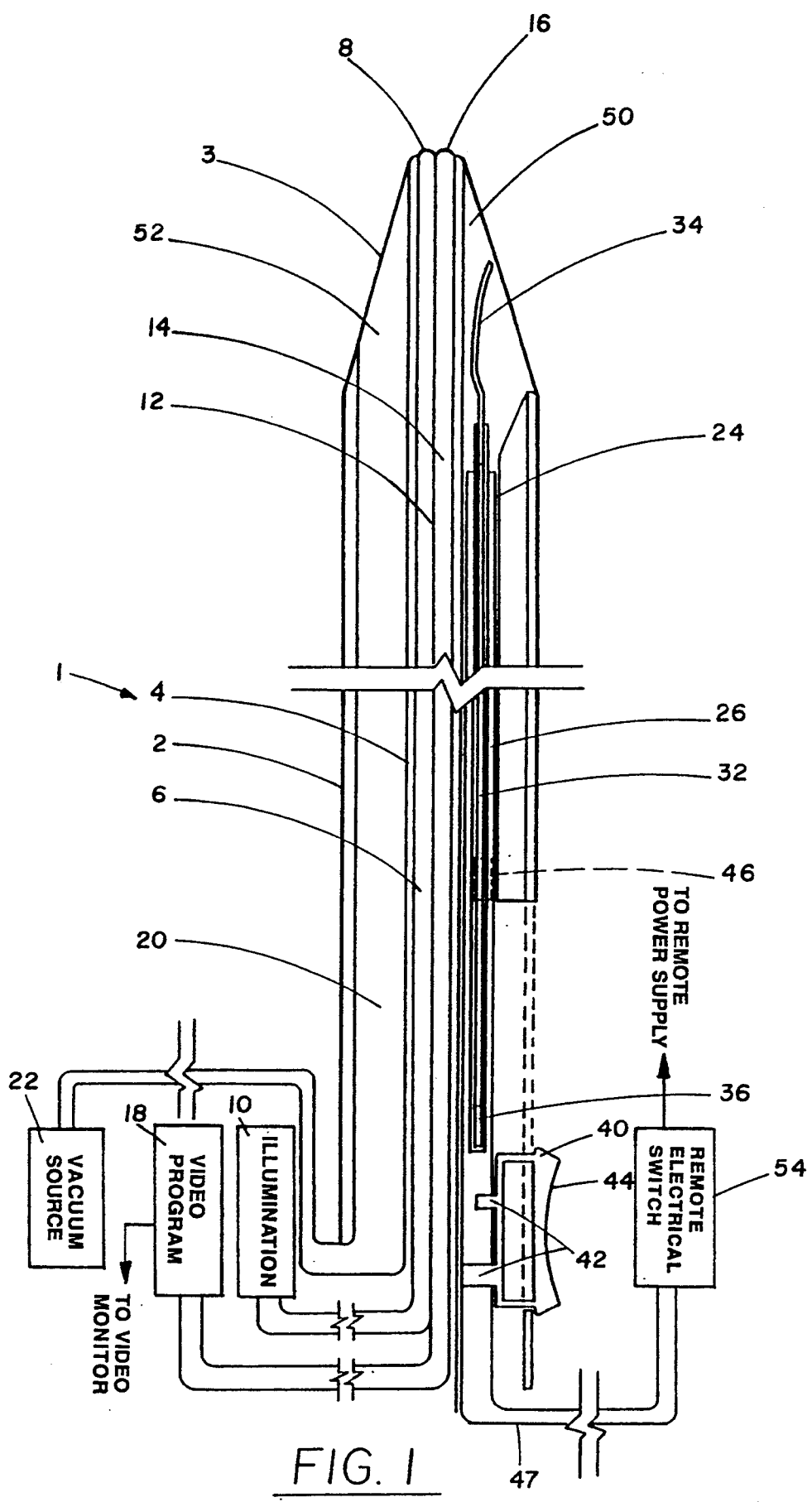
FIG. 1 is a cross-section of the multi-function cauterizing instrument of the present invention in the at rest condition with cauterizing tips de-energized.
Figure 2:
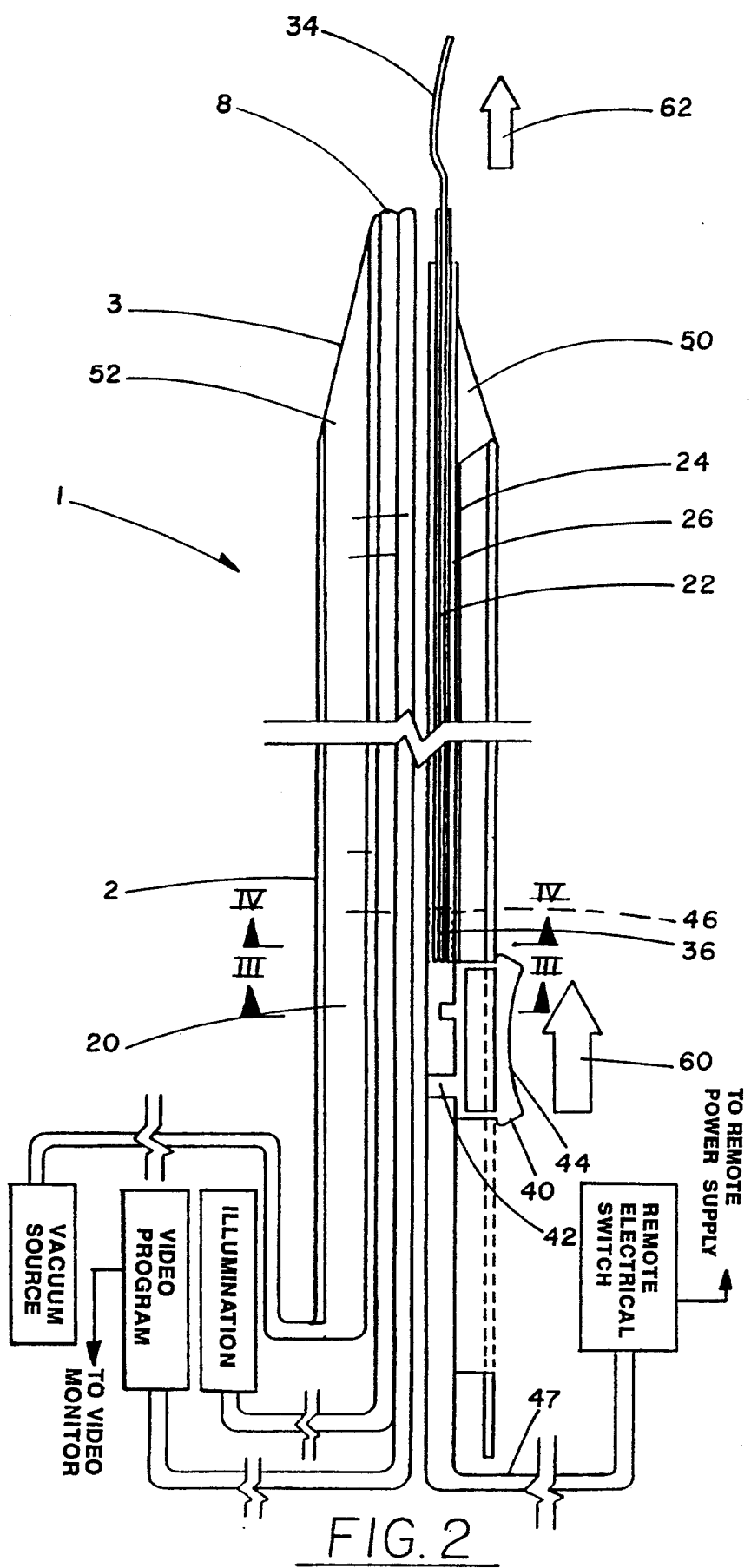
FIG. 2 is a cross-section of the cauterizing instrument with a cauterizing tip selectively advanced and energized to cauterize a patient's tissue.

The multiple function cauterizing instrument 1 which forms the present invention is now described while referring to the drawings, where FIGS. 1 and 2 show a cross section of the instrument 1 having a generally cylindrical housing 2 and a conically-shaped nose 3 at one end of the housing. The housing 2 is preferably manufactured from a reinforced plastic material. Cauterizing instrument 1 has a plurality of parallel aligned, longitudinally extending passageways extending therethrough. More particularly, a first passageway 4 includes an illumination optical fiber 6. Illumination fiber 6 extends from a suitable lens 8 at the front of the conical nose 3 of cauterizing element 1, through housing 2, to a source of illumination 10. The source of illumination 10 is a conventional high intensity lamp, such as a halogen lamp, or the like, which is known in the art to be capable of focusing light into the illumination optical fiber 6. By virtue of the foregoing, high intensity incident light signals can be supplied by the source 10 and focused by lens 8 at a patient's tissue area to be cauterized by instrument 1.

A second passageway 12 extends longitudinally through the housing 2 of cauterizing instrument 1 and includes a viewing optical fiber 14. Viewing optical fiber 14 extends from a suitable wide angle camera lens 16 that is located adjacent lens 8 at the front of conical nose 3 to a conventional remote video program processor 18. The video program processor 18 is connected to a commercially available video monitor. The video program processor 18 is capable of converting optical output signals supplied thereto from viewing optical fiber 14 and lens 16 into a visual image for display at the video monitor. By virtue of the foregoing, the surgeon will be able to accurately view the patient's tissue to be cauterized that is illuminated by illumination optical fiber 6 via lens 8.

A relatively wide exhaust channel 20 also extends longitudinally through the housing 2 of cauterizing instrument 1 from an intake vent 52 (best shown in FIG. 10) at the nose 3 to a remote vacuum source 22. Vacuum source 22 is commonly available at most hospitals in operating and similar rooms where cauterizing procedures are likely to be performed. The vacuum source 22 is typically hand or foot controlled by the surgeon so that a suction force may be selectively generated within exhaust channel 20. By virtue of the foregoing, potentially view-obstructing exhaust gases, fumes and smoke that are produced when the patient's tissue is cauterized and burnt will be removed from the surgeon's field of view and evacuated through exhaust channel 20 for disposal at vacuum source 22.

Figure 3:
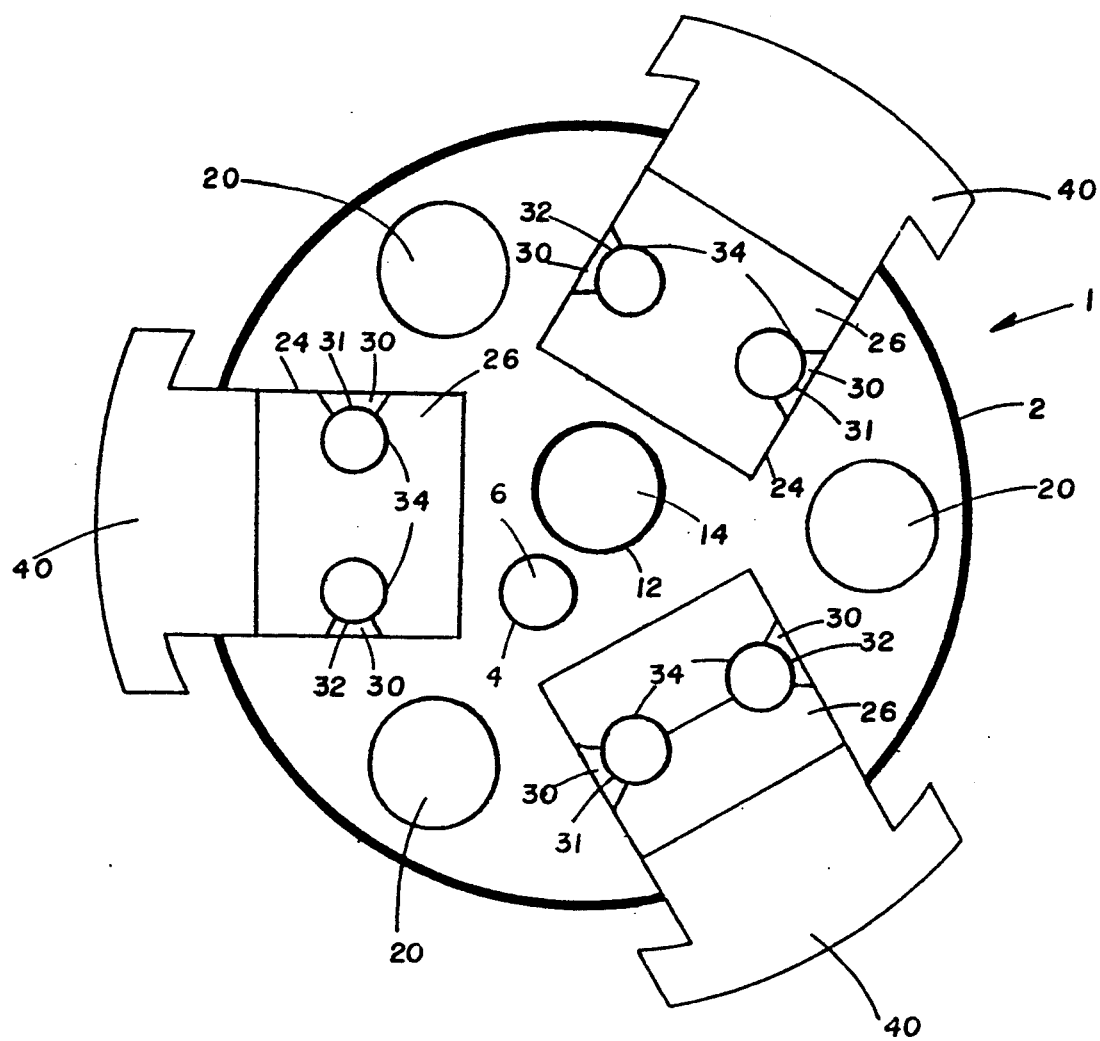
FIG. 3 is a cross-section taken along lines 3—3 of FIG. 2.
Figure 4:
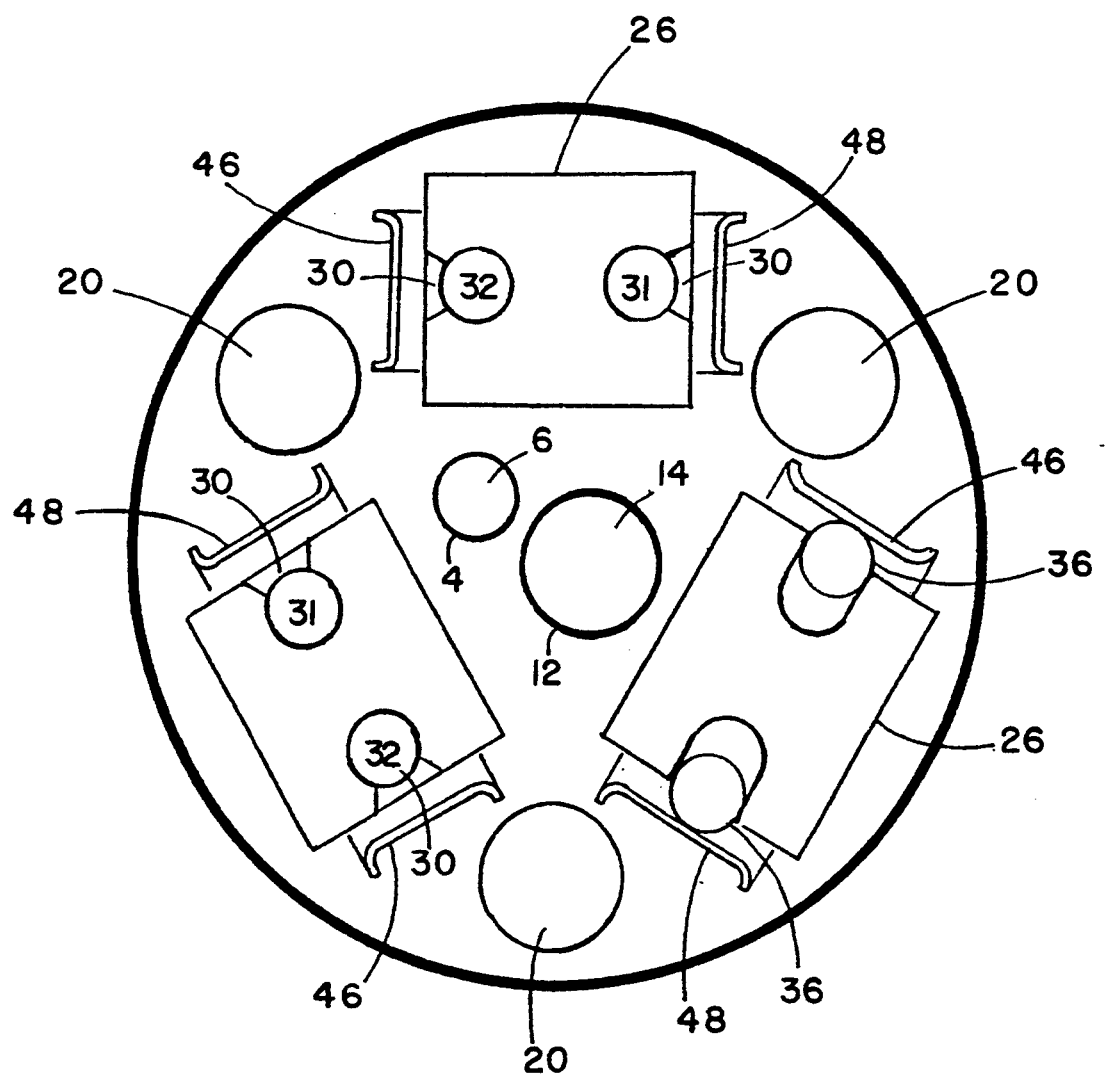
FIG. 4 is a cross-section taken along lines 4—4 of FIG. 2.

In accordance with an important aspect of the present invention, a series of guide channels 24 (only one of which being shown in FIGS. 1 and 2) extend longitudinally through the housing 2 of cauterizing instrument 1. As is best shown in FIGS. 3 and 4, instrument 1 includes three such guide channels 24 that are uniformly spaced from one another at 120 degree intervals around the body 2. However, the precise number of guide channels 24 and soon-to-be-described guide rails 26 that are slidably received within channels 24 are not to be considered as limitations of this invention.

The guide rails 26 which are received within and slidable axially through respective guide channels 24 in housing 2 of cauterizing instrument 1 are now described while referring concurrently to FIGS. 1 and 5 of the drawings. Each guide rail 26 (only one of which being shown in FIGS. 1 and 2) includes an elongated, rectangular carrier 28 that is preferably manufactured from a non-conductive plastic material. An opposing pair of longitudinally extending slots 30 (best shown in FIGS. 3 and 4) are formed along the sides of carrier 28 of guide rail 26. Extending through the slots 30 in carrier 28 are a pair of electrically conductive (e.g. stainless steel) rods 31 and 32. The rods 31 and 32 are recessed and electrically isolated within slots 30. First ends of the pair of rods 31 and 32 project axially and outwardly past the front of carrier 28 at which said rods are connected to a heating element or cauterizing tip 34, which is typically a wire of narrow diameter manufactured from a conductive material, such as nichrome, or the like. The opposite ends of the pair of rods 31 and 32 have a bowed or arcuate contact 36 formed thereon. The arcuate electrical contacts 36 of rods 31 and 32 project radially outward from the ends of slots 30 at relatively wide openings 38 formed in the sides of carrier 28 which accommodate the contacts 36. The advantage of the arcuate contacts 36 of rods 31 and 32 projecting radially outward from the slots 30 formed in carrier 28 will be described hereinafter.

Extending upwardly from the top of carrier 28 of guide rail 26 is a position control button 40 that is affixed to carrier 28 by means of a pair of pins (designated 42 in FIGS. 1 and 2). Molded into the position control button 40 is a thumb pad 44 that is shaped to comfortably receive the thumb of the surgeon.

Figure 8:
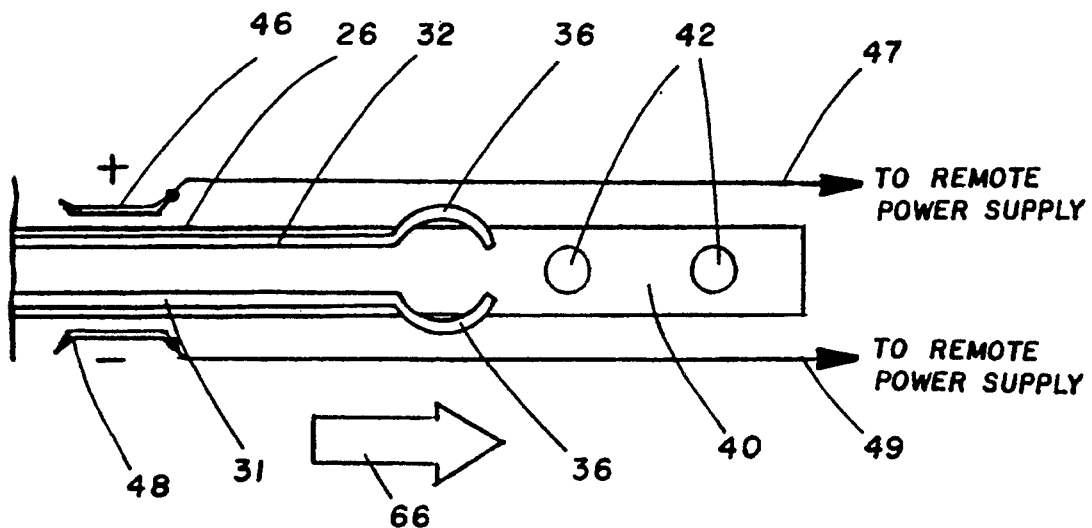
FIGS. 8 and 9 show the electrical connections for de-energizing and energizing the cauterizing tip carried by the guide rail of FIG. 5.

In the at rest condition of cauterizing instrument 1 (shown in FIG. 1), the guide rail 26 is located in a relatively retracted position within its respective guide channel 24. That is to say, the cauterizing tip 34 of guide rail 26 is withdrawn inwardly of exit opening 50 so as to be shielded within the housing 2 of instrument 1. Moreover, the electrically conductive rods 31 and 32 of guide rail 26 are isolated and thereby disconnected from a source of electrical power so that cauterizing tip 34 can not be energized and is incapable of producing heat. More particularly, a pair of positive and negative power terminals 46 and 48 (best shown at FIG. 8) is .Located along opposite sides of each guide channel 24 in which guide rail 26 is slidably received. Power terminals 46 and 48 are connected to a remote power supply in the operating room via wires 47 and 49 and a remote switch 54 such as a manually (e.g. foot) controlled switch. Power terminals 46 and 48 are aligned to engage and thereby provide electrical power to the conductive rods 31 and 32 of guide rails 26 when the radially projecting electrical contacts 36 of rods 31 and 32 are moved into electrical connection with respective power terminals 46 and 48 at guide channel 24.

Figure 9:
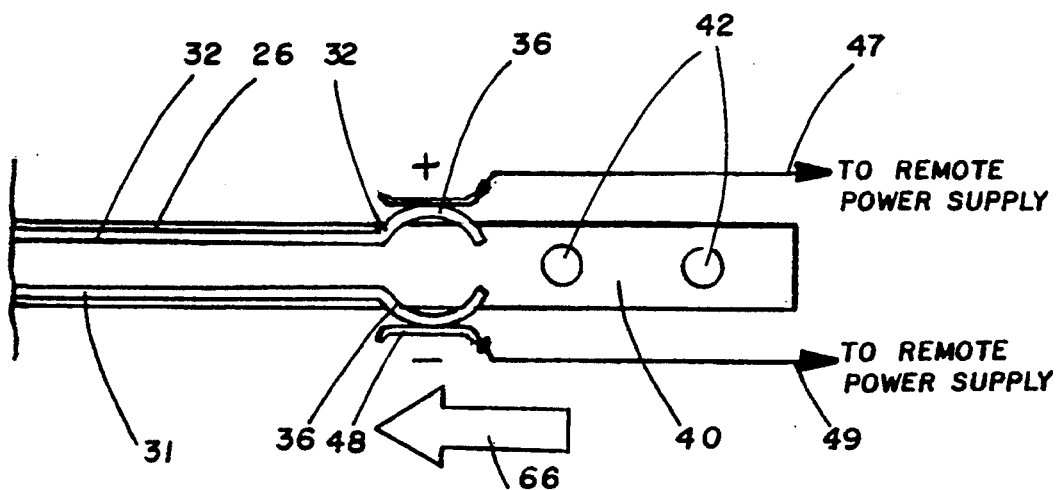
Figure 10:
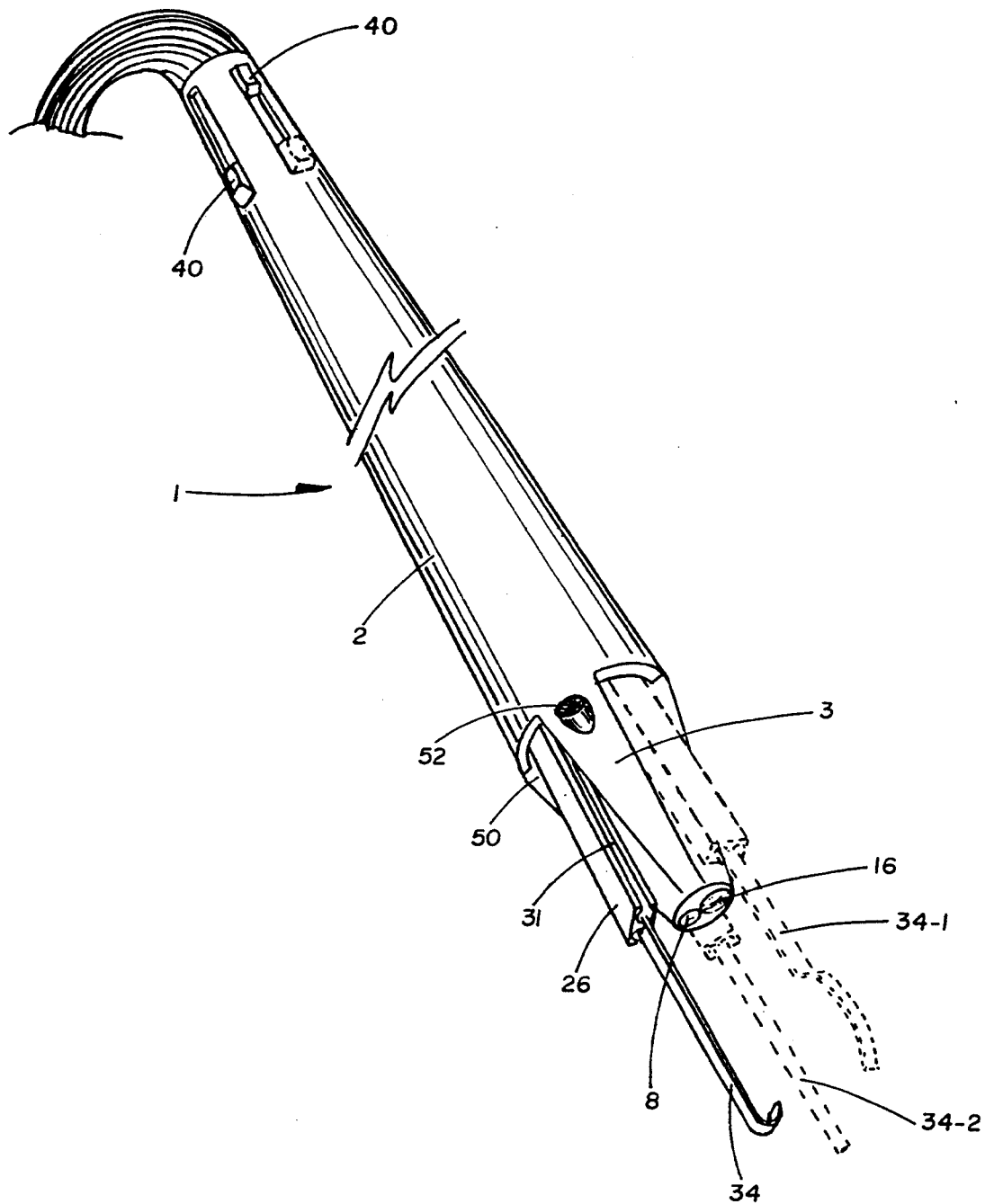
FIG. 10 is a perspective view of the cauterizing instrument with a cauterizing tip selectively and outwardly advanced therefrom.

To this end, and as best shown in FIGS. 2 and 9, the surgeon can selectively move guide rail 26 to an axially extended position through guide channel 24 to advance cauterizing tip 34 outwardly of housing 2 and into contact with the targeted tissue area of the patient. That is to say, the surgeon places his thumb on the thumb pad 44 of position control button 40 and applies an axially directed force thereto (in the direction of the reference arrow 60) for causing the guide rail 26, to which button 40 is attached, to slide through channel 24. Accordingly, and as shown in FIGS. 2 and 10, the cauterizing tip 34 will be moved past the exit opening 50 in the nose 3 of instrument 1. As the guide rail 26 is moved through guide channel 24 (in the direction of the reference arrow 62), the radially projecting contacts 36 of conductive rods 31 and 32 are simultaneously moved through guide channel 24 (in the direction of reference arrow 64 of FIG. 9) and into electrical connection with the power terminals 46 and 48 at opposite sides of channel 24. Thus, electrical power may be applied to conductive rods 31 and 32 at contacts 36 to energize the cauterizing tip 34 so that said tip can be heated for cauterizing the patient's tissue.

By virtue of the present invention, the surgeon has easy access to any one of the plurality of cauterizing tips (designated 34-1 and 34-2 in FIGS. 6 and 7). That is to say, the surgeon may return cauterizing tip 34 to its shielded and de-energized position of FIG. 1 within the housing 2 of cauterizing instrument 1 by sliding guide rail 26 to its retracted position in guide channel 24 so as to separate (in the direction of reference arrow 66 of FIG. 8) contacts 36 from power terminals 46 and 48. The surgeon may then selectively advance, in the manner just described, any one of the other guide rails and the cauterizing tip 34-1 or 34-2 associated therewith to the axially extended position (shown in phantom lines in FIG. 10) depending upon the function to be performed. However, it should be appreciated that all of the cauterizing tips 34, 34-1 and 34-2 are carried by guide rails that may be advantageously and conveniently carried within the housing 2 of a single cauterizing instrument 1, whereby to eliminate the need and expense associated with the multiple cauterizing wands that are common to conventional cauterizing techniques.

Likewise, the presently disclosed multiple function cauterizing instrument 1 includes optical means to both illuminate and view the patient's targeted tissue area and means to exhaust fumes and gases caused by burning tissue at the target site so as to prevent obstruction of the surgeon's view. Hence, the illuminating, viewing and exhausting functions may be efficiently performed by a single medical professional (i.e. without the aid of an assistant) using a single instrument, whereby to avoid the need for making multiple incisions through the patient's tissue as might otherwise be required to accommodate the conventional viewing, illuminating and exhausting tools that are commonly used in conventional cauterizing techniques.

It will be apparent that while a preferred embodiment of the invention has been shown and described, various modifications and changes may be made without departing from the true spirit and scope of the invention.

Having thus set forth the preferred embodiment of the invention, we claim:

1. A cauterizing instrument including at least one heating element at which heat is generated to cauterize a patient's tissue, said instrument comprising:
   a housing;
   support means to which said heating element is attached, said support means slidably received within said housing;
   means by which to slide said support means through said housing between a retracted position at which said heating element is completely surrounded and shielded from contact with the patient's tissue by said housing and an extended position at which said heating element is advanced outwardly from said housing for contacting the patient's tissue and generating the heat to cauterize said tissue;
   a pair of electrically conductive rods carried by said support means and connected to said heating element; and
   first and second power terminals located within said housing and connected to a source of electrical power, said power terminals positioned relative to said support means so as to be electrically connected to said pair of conductive rods to provide power to said heating element when said support means slides through said housing to said extended position and said heating element is advanced outwardly from said housing,
   said first and second power terminals being disconnected from said pair of conductive rods to de-energize said heating element when said support means slides through said housing to said retracted position and said heating element is shielded by said housing.

2. The cauterizing instrument recited in claim 1, further comprising another support means having a second heating element attached thereto, said other support means being slidably received within said housing; and
   additional means by which to slide said other support means through said housing between a retracted position at which said second heating element is shielded by said housing and an extended position at which said second heating element is advanced outwardly from said housing for contacting the patient's tissue.

3. The cauterizing instrument recited in claim 2, wherein the first and second heating elements of said respective support means are conductive wires that are shaped differently from one another.

4. The cauterizing instrument recited in claim 2, further comprising first and second exit openings formed in said housing, said first and second heating elements being selectively advanced outwardly from said housing to contact the patient's tissue via respective ones of said first and second exit openings.

5. The cauterizing instrument recited in claim 1, wherein the means by which to slide said support means through said housing to shield or advance said heating element is a position control button affixed to said support means and manually accessible for receiving an axially directed force.

6. The cauterizing instrument recited in claim 1, wherein said pair of conductive rods are recessed within said support means, each of said rods having an electrical contact projecting radially outward from said support means to be connected to respective ones of said first and second power terminals when said support means slides to said extended position and said heating element is advanced outwardly from said housing.

7. The cauterizing instrument recited in claim 1, further comprising an exhaust channel extending through said housing for connection to a source of vacuum such that gas and fumes generated during cauterizing the patient's tissue can be suctioned away from the tissue.

8. The cauterizing instrument recited in claim 7, further comprising an intake vent formed in said housing and communicating with said exhaust channel such that the gas and fumes generated during cauterization are suctioned by said source of vacuum via said intake vent and said exhaust channel.

9. The cauterizing instrument recited in claim 1, further comprising a lens located at one end of said housing and optical transmission means extending through said housing between said lens and a source of light such that incident light from said source is supplied to the patient's tissue to be cauterized by way of said optical transmission means and said lens.

10. The cauterizing instrument recited in claim 9, wherein said optical transmission means is an optical fiber.

11. The cauterizing instrument recited in claim 1, further comprising a lens located at one end of said housing and optical transmission means extending through said housing between said lens and a video monitor such that a visual image of the patient's tissue to be cauterized is supplied to the monitor by way of said lens and said optical transmission means.

12. The cauterizing instrument recited in claim 11, wherein said optical transmission means is an optical fiber.

13. The cauterizing instrument recited in claim 11, wherein said lens is a wide angle camera lens.

14. A cauterizing instrument including a housing and comprising:

at least one heating element to cauterize a patient's tissue;

support means connected to said heating element and slidably received within said housing;

means by which to slide said support means through said housing between a retracted position at which said heating element is shielded by said housing and an extended position at which said heating element is advanced outwardly from said housing for contacting the patient's tissue;

a pair of electrically conductive rods carried by said support means and connected to said heating element;

first and second power terminals located within said housing and connected to a source of electrical power, said power terminals positioned relative to said support means so as to be electrically connected to said pair of conductive rods to provide power to said heating element when said support means slides through said housing to said extended position and said heating element is advanced outwardly from said housing, said first and second power terminals being disconnected from said pair of conductive rods to de-energize said heating element when said support means slides through said housing to said retracted position and said heating element is shielded by said housing;

lens means located at one end of said housing;

optical transmission means extending through said housing from said lens means for transmitting optical signals; and an exhaust channel extending through said housing to be connected to a source of vacuum such that gas and fumes generated during cauterizing the patient's tissue can be suctioned away from the tissue.

15. The cauterizing instrument recited in claim 14, wherein said pair of conductive rods are recessed within said support means, each of said rods having an electrical contact projecting radially outward from said support means to be connected to respective ones of said first and second power terminals when said support means slides to said extended position and said heating element is advanced outwardly from said housing.

16. The cauterizing instrument recited in claim 14, wherein said lens means includes first and second lenses and said optical transmission means includes a first optical fiber extending through said housing from said first lens to a light source for providing incident light to the tissue to be cauterized and a second optical fiber extending through said housing from said second lens to a video monitor for providing a visual image to said monitor of the tissue to be cauterized.

17. A cauterizing instrument including at least one heating element at which heat is generated to cauterize a patient's tissue, said instrument comprising:

a housing;

support means to which said heating element is attached, said support slidably received within said housing;

means by which to slide said support means through said housing;

a pair of electrically conductive contacts carried by said support means and connected to said heating element; and first and second power terminals located on said housing and connected to a source of electrical power, said power terminals positioned relative to said support means so as to be electrically connected to said pair of conductive contacts to provide power to said heating element when said support means slides in a first direction through said housing, said first and second power terminals being disconnected from said pair of conductive contacts to de-energize said heating element when said support means slides in an opposite direction through said housing.

18. The cauterizing instrument recited in claim 17, wherein said pair of conductive contacts are first and second elongated rods that are recessed within said support means, each of said rods having an electrically conductive area projecting in a direction radially outward from said support means to be connected to respective ones of said first and second power terminals when said support means slides in said first direction through said housing.

* * * * *